United States Patent [19]
Moss et al.

[11] Patent Number: 5,425,173
[45] Date of Patent: Jun. 20, 1995

[54] METHOD OF RESUPPLYING NEW REPLACEMENT TUBING IN A MEDICAL CASSETTE FOR AMBULATORY MEDICAL INFUSION PUMPS

[75] Inventors: Richard Moss, West Bloomfield; Fredrick L. Erlich, Farmington Hills, both of Mich.

[73] Assignee: Fredrick Kamienny, West Bloomfield, Mich.

[21] Appl. No.: 134,046

[22] Filed: Oct. 12, 1993

[51] Int. Cl.6 .............................. B23P 15/00
[52] U.S. Cl. ..................... 29/888.021; 29/402.08; 604/131; 604/151; 604/250
[58] Field of Search ............. 604/131, 151, 250; 417/474, 477, 475, 476; 29/888.021, 402.03, 402.08, 402.09

[56] References Cited

U.S. PATENT DOCUMENTS

| | | |
|---|---|---|
| D. 232,085 | 7/1974 | Saratoga ............... D24/111 |
| D. 247,820 | 5/1978 | Stuetzer ............... D24/111 |
| D. 294,733 | 3/1988 | Peterson et al. ......... D24/8 |
| D. 326,153 | 5/1992 | Eastman et al. ......... D24/111 |
| 4,187,057 | 2/1980 | Xanthopoulos . |
| 4,256,437 | 3/1981 | Brown . |
| 4,274,407 | 6/1981 | Scarlett . |
| 4,282,867 | 8/1981 | Du Toit ............... 604/151 |
| 4,337,769 | 7/1982 | Olson ................. 604/131 |
| 4,398,908 | 8/1983 | Siposs . |
| 4,451,255 | 5/1984 | Buyar et al. .......... 604/151 |
| 4,468,221 | 8/1984 | Mayfield . |
| 4,559,038 | 12/1985 | Berg et al. . |
| 4,565,542 | 1/1986 | Berg . |
| 4,569,674 | 2/1986 | Phillips et al. . |
| 4,650,469 | 3/1987 | Berg et al. . |
| 4,667,854 | 5/1987 | McDermott et al. . |
| 4,684,364 | 8/1987 | Sawyer et al. ......... 604/151 |
| 4,845,487 | 7/1989 | Frantz et al. . |
| 4,978,335 | 12/1990 | Arthur, III . |
| 5,032,112 | 7/1991 | Fairchild et al. ....... 604/151 |
| 5,098,387 | 3/1992 | Wiest ................. 604/131 |
| 5,106,374 | 4/1992 | Apperson et al. ....... 604/131 |
| 5,213,483 | 5/1993 | Flaherty et al. . |
| 5,219,327 | 6/1993 | Okada ................ 604/151 |
| 5,242,407 | 9/1993 | Struble et al. ......... 604/131 |

FOREIGN PATENT DOCUMENTS 9310853 6/1993 WIPO ................ 604/151

*Primary Examiner*—Irene Cuda
*Attorney, Agent, or Firm*—Reising, Ethington, Barnard, Perry & Milton

[57] ABSTRACT

A method for resupplying a remote cassette assembly (14) for an ambulatory medical infusion pump (10) with a new replacement tube (22a) includes the steps of disassembling a used tube assembly (22) from the cassette assembly (14) by removing a luer lock (34) located at the end of microbore tubing (32) by severing the tubing (22), removing the tubing (22) by passing it through apertures (30), (25) and (47) in the cassette assembly (14), inserting a new unused tubing (22a) into the access slot (40) to the interior of said cassette, and by inserting tubing (22a) such that the tubing (22a) is pulled through the apertures (47), (25) and (30).

6 Claims, 2 Drawing Sheets

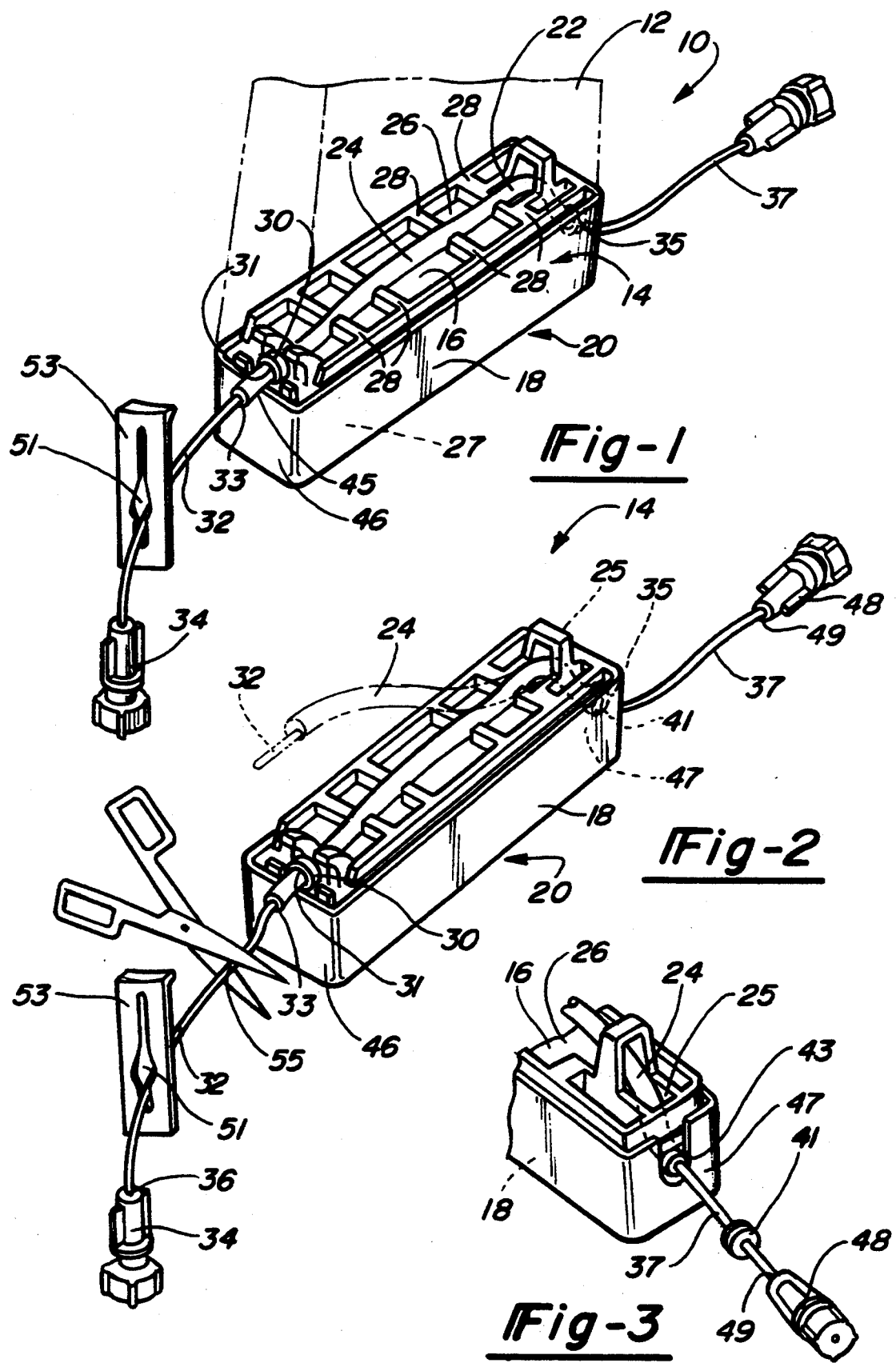

METHOD OF RESUPPLYING NEW REPLACEMENT TUBING IN A MEDICAL CASSETTE FOR AMBULATORY MEDICAL INFUSION PUMPS

TECHNICAL FIELD

The field of this invention relates to a method of recycling cassettes for ambulatory medical infusion pumps.

BACKGROUND OF THE DISCLOSURE

Ambulatory medical infusion pumps are a commercially successful and popular medical instrument. The pumps allow for the convenient continuous and calibrated delivery of a variety of medicines including but not limited to antibiotics, pain relieving drugs, and chemotherapy drugs.

The pumps have a fastener system that allows a supply tube to be removably attached to the pump. The supply tube can be installed on a cassette that has a soft pliable drug reservoir bag placed within a hard shell made from a rigid plastic such as poly-carbonate to protect the integrity of the bag. The supply tube has a soft section positioned within the pump assembly which is squeezed between the pump and the cassette pump plate to draw or pump the medicine through the supply tube.

The soft tube section is attached to microbore tubing that exits the pump assembly. The microbore tubing has a luer lock or similar connector attached to its distal end that allows connection to a intravenous infusion or subcutaneous delivery system. The microbore tubing resists any unintentional kinking or crimping thus assuring proper delivery of the drugs therethrough.

The pump plate of the pump cassette is permanently secured either by adhesive or sonic welding to the cassette shell to assure that the shell is not unintentionally removed from about the bag so that the bag does not become accidentally exposed and maintains its integrity against accidental puncture.

Often larger amounts of medicine are needed by the patient. Instead of numerous cassettes with a small bag in each cassette, a larger remote bag of medicine is used. The cassette that attaches to the pump includes only a soft supply tube that engages the pump, a microbore outlet tube that attaches to the patient, and a microbore inlet tube that attaches to the remote bag. The inlet tube and outlet tube have distal ends permanently attached to fittings such as luer locks. The fittings maintain the tube assembly permanently secured to the cassette. The microbore tubes are permanently connected to opposing ends of the supply tube. The cassette is constructed to permanently retain the supply tube in place. This cassette assembly is often referred to as a remote reservoir cassette or remote cassette.

When the medicine needs to be changed, one supply bag is easily disconnected from the pump cassette and another supply bag with a second medicine is conveniently attached to the pump cassette.

Because the supply tube has been in fluid contact with a patient, the used remote cassette may contain bodily fluids that passed up through the tubing from the patient. Thus, the tubing is considered medical waste and must be disposed of accordingly. Many principalities now have laws that forbid medical waste from being placed in landfills. The preferred disposal method is by incineration. For proper incineration, the cassette with both the spent tube and hard shell need to be incinerated at relatively high temperatures compared to regular incineration temperatures of other waste products. The higher temperatures are needed for the proper decomposition of certain chemotherapy drugs and for certain rigid plastics such as poly-carbonate. The cassette shell is incinerated with the reservoir bag, even through the cassette shell can be easily resterilized and capable of storing another tube for reuse with the pump.

The pumps are constructed for long durability. the pump thus can be used with many cassettes during its useful life over several years.

The increasing expense and difficulties of proper disposal of the cassette assembly necessitates that only the waste be disposed of and other parts be repaired and reused when possible and convenient. The reuse of the cassette shell can save much plastic and reduce the amount of unnecessary incineration and the unwanted particulates and gasses produced by incineration. What is needed is a method of removing the spent supply tube and fittings and reinstalling a new supply tube and fitting on the cassette shell.

SUMMARY OF THE INVENTION

In accordance with one aspect of the invention, a method for removing spent tubes and resupplying a cassette for an ambulatory medical infusion pump with a new tube is provided. The method includes the steps of removing a lock fastener located at the end of a tube installed on the cassette preferably by cutting the tube, removing the spent tube from the cassette and installing a new tube onto the cassette.

Preferably the cassette has a pump plate with a cassette shell secured about the peripheral edge of the plate. The cassette shell and cassette pump plate each have an aperture therethrough with the tube passing through the apertures and through the interior of the shell. In one embodiment the pump plate has a guide ring defining an aperture therethrough which receives the tube therethrough. The used tube is removed from the guide ring aperture and the two apertures through the pump plate and cassette shell and removed from the interior of the cassette after the lock fastener is cut from the tube.

The new replacement tube is inserted through the cassette shell aperture and pump plate aperture and extended through the interior of the shell before the lock fastener is secured to the replacement tube.

According to a broader aspect of the invention, the tube assembly is cut between its two distal ends between the permanently attached lock fastener to form two tube fragments. At least one tube fragment is slid out through an aperture in said cassette to disengage it from the cassette. A new replacement tube is then installed with the cassette.

BRIEF DESCRIPTION OF THE DRAWINGS

Reference now is made to the accompanying drawings in which:

FIG. 1 is a perspective view of a remote reservoir assembly attachable to a pump (shown in phantom);

FIG. 2 is a perspective view of the remote cassette assembly with the luer lock shown being cut off;

FIG. 3 is a perspective view showing the used tube being removed through the apertures through the shell aperture;

DETAILED DESCRIPTION OF THE PREFERRED EMBODIMENT

Figure 4:
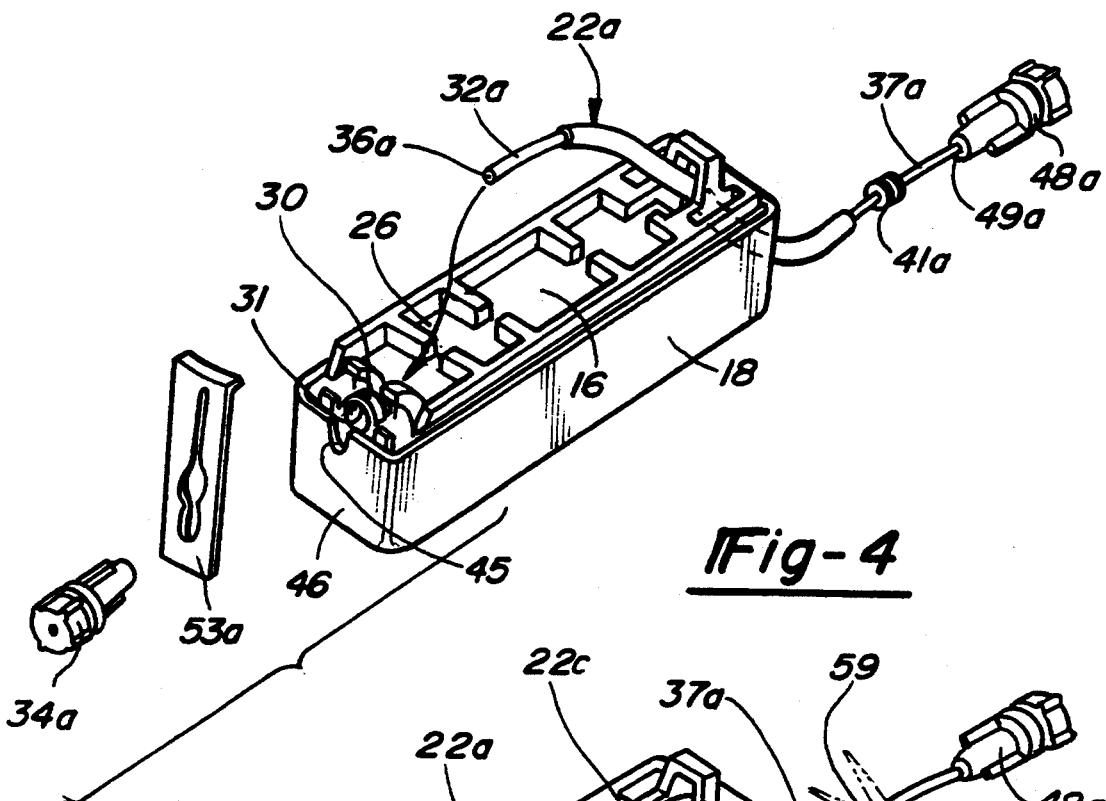
FIG. 4 is a view similar to FIG. 2 showing a new replacement tube being installed onto the cassette shell.

Referring now to FIGS. 1 and 2, an ambulatory medical infusion pump assembly 10 includes a pump housing 12 and a known remote reservoir cassette 14 removably attached to the housing 12. The cassette assembly 14 has a pump plate 16 sonically welded to a cassette shell 18 that together forms a cassette casing 20 which includes an interior chamber 27. A tube assembly 22 includes a pliable tube section 24 positioned against the exterior side 26 of the pump plate 16. Appropriate guides 28 and tube ring retainer 30 retain the tube 24 in its proper position against plate 16. The retainer 30 forms an aperture 31 through which tube section 24 extends. At each end 33 and 35, the tube 24 is connected to a microbore tubing 32 and 37 that extends from the pump housing 12 and cassette casing 20. Tube end 33 extends from a slot 45 in outlet end 46 of shell 18. The tube 32 also extends through a tapered slot 51 in a plastic clamp 53. Tube end 35 extends through apertures 25 through the interior 27 to a rubber gasket 41 installed in the slot 43 in inlet end 47 of shell 18, as shown in FIG. 4.

A Luer lock 34 is connected at the distal end 36 of the microbore tubing 32 to be connected to infusion tubing (not shown). A similar complementary lock fastener 48 is connected at distal end 49 of microbore tubing 37. The lock fasteners 34 and 48 are permanently secured to the tubing 32 and 37 respectively and the tubing 32 and 37 are permanently bonded to the soft tubing section 24. The lock fasteners 34 and 48 are sized larger than slot 43, aperture 25 and aperture 31 to provide installation of the tube assembly 22 resistant to inadvertent disassembly.

Referring now particularly to FIG. 2, the cassette assembly 14 is detached in the conventional fashion from the pump housing 12. Instead of the whole cassette assembly 14 being discarded, the tubing 32 is cut by scissors between cassette shell 18 and clamp 53 as indicated at position 55. The cut is made as close as practical to the shell 18.

The tube 24 and the attached fragment of microbore tubing 32 is then removed by being pulled through retainer ring aperture 31, through the tube port 25 into the interior 27 and out again through slot 45 as shown in FIG. 3.

Figure 5:
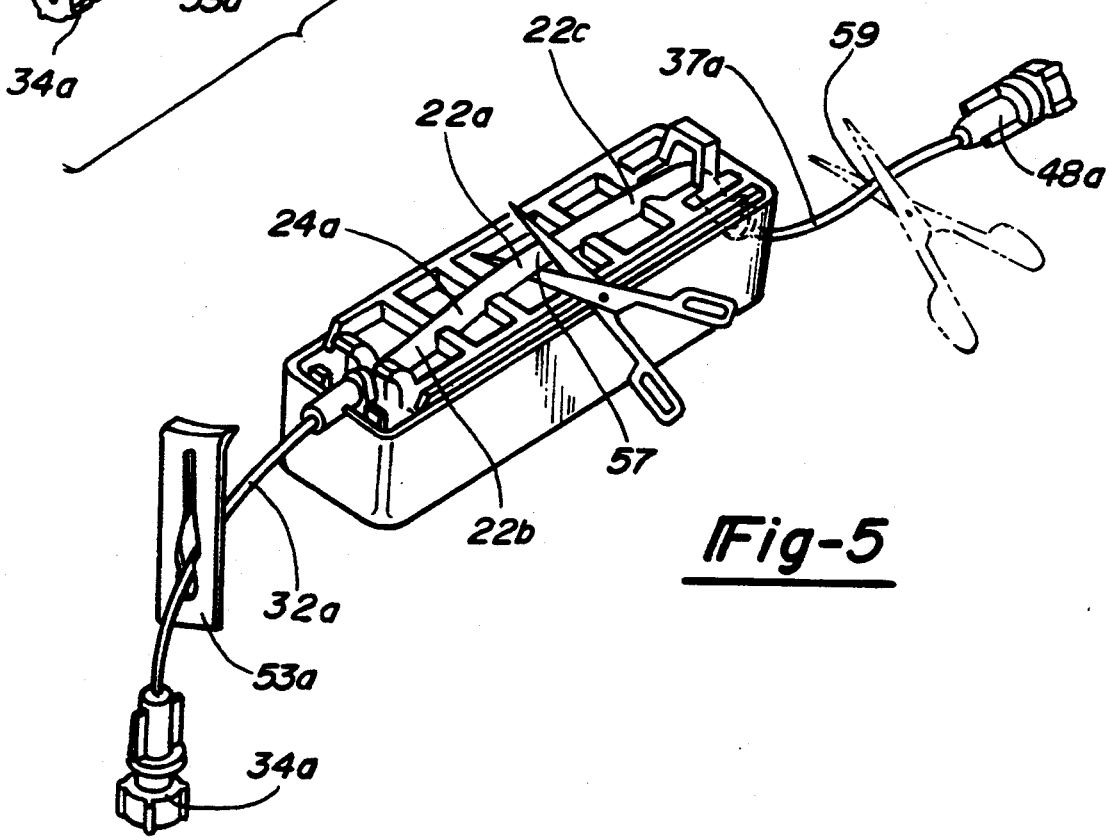
FIG. 5 is a view similar to FIG. 4 illustrating the cassette shell having a new replacement tube installed thereon.

The used tube assembly 22, after being completely disassembled from the shell 18 and pump slot 16, is then properly disposed as medical waste. As illustrated in FIGS. 4 and 5, a new replacement tube assembly 22a is then installed and assembled on cassette assembly 14. The replacement microbore tubing 32a and 37a preattached to the replacement tube and threaded through the slot 45 into interior 27 and back out through the tube port 25. The tubing 22a is then pulled through the aperture 31 of retainer ring 30. Replacement Luer lock 34a is then secured on the distal end 36a of the tubing 32a. Replacement gasket 41a is slipped onto tubing 37a and replacement fastener 48a is secured on distal end 49a of tubing 37a. The gasket 41a and replacement fastener 48a may be pre-installed on tubing 37a before the installation of the tubing 22a on cassette assembly 14.

At this point, the cassette assembly 14, as shown in FIG. 5, is packaged and sterilized under either standard radiation procedures or ethyleneoxide gas sterilization procedures and ready for sequential use. In this fashion, a medical cassette casing 20 can be repaired and re-used with replacement tubing 22a. Further use of the cassette casing 20 with third and subsequent replacement tubing 22a can be accomplished by repeating the above described method.

As shown in FIG. 5, the severing of tube 22 or 22a can be made as well at other locations of tubing 22 or 22a. The tubing section 24 may be cut as indicated at 57 to produce two tube fragments 22b and 22c, one fragment 22b being pulled out of aperture 30 and the other tube fragment 22c being pulled out through aperture 25 and slot 43.

The tubing 22a may alternately be severed along microbore tubing 37 as indicated at 59.

The tubing is then pulled out in the opposite direction as described above for FIG. 2. Installation of the new replacement tube 22a remains unchanged from that described above.

Of course, the severing of tube 22, 22a may be accomplished by cutting with a scissors, shearing, slicing by a knife, melting the tube with a hot wire, ripping by pulling apart the tubing, dissolving the tubing by chemicals or other practical methods of severing into two pieces.

It is also foreseen that a chemical solvent can be applied to one of the luer locks 34 or 48 to remove the lock from tubing 22 or 22a.

The invention has been described in an illustrative manner, and it is to be understood that the terminology which has been used is intended to be in the nature of words of description rather than of limitation.

Variations and modifications are possible without departing from the scope and spirit of the present invention as defined by the appended claims.

The embodiments in which an exclusive property or privilege is claimed are defined as follows:

1. A method of resupplying a used remote cassette for an ambulatory medical pump with a new supply tube, said cassette having an inlet and an outlet end with a pump plate therebetween, and a spent supply tube extending through said inlet end and outlet end and engaged on said pump plate, said spent supply tube having a first lock fastener located at a first end of said tube and a second lock fastener at a second end of said tube, said used tube passing through an aperture on said cassette that forms a tube retainer with said first and second lock fasteners being larger than said aperture of said tube retainer, said method characterized by;
   removing said first lock fastener located at one end of said spent tube that has been previously install to said cassette;
   removing said spent tube from said cassette by sliding it through said tube retainer on said cassette;
   inserting a new replacement tube through said tube retainer on said cassette;
   connecting a first replacement lock fastener on said first end of said new tube; and
   connecting a second lock fastener on a distal end of said tube after inserting said tube through said tube retainer aperture.

2. A method as defined in claim 1 further characterized by:
   said cassette having an outer peripheral wall with an aperture therethrough leading to an interior thereof;

said spent tube extending through said aperture and through said interior of said cassette;

said spent tube being removed from said aperture after said first lock fastener is removed and said new tube being inserted through said aperture before said second lock fastener is secured to said new tube.

3. A method as defined in claim 2 further characterized by:

said cassette includes a pump plate with a raised tube retainer forming a guidance aperture through which a tube extends;

said used tube being removed from said guidance aperture after said first lock fastener is removed and said new replacement tube being inserted through said guidance aperture before said second lock fastener is secured to said new replacement tube.

4. A method as defined in claim 1 further characterized by:

said cassette includes a pump plate with a raised tube retainer forming a guidance aperture through which a tube extends;

said used tube being removed from said guidance aperture after said first lock fastener is removed and said new replacement tube being inserted through said guidance aperture before said second lock fastener is secured to said new replacement tube.

5. A method as defined in claim 4 further characterized by:

said lock fastener being removed by severing said used tube at a section between said cassette and said lock fastener.

6. A method as defined in claim 1 further characterized by:

said lock fastener being removed by severing said used tube at a section between said cassette and said lock fastener.

* * * * *